United States Patent
Allmendinger et al.

(10) Patent No.: US 8,611,987 B2
(45) Date of Patent: Dec. 17, 2013

(54) METHOD AND DEVICE FOR ASSISTING IN DETERMINATION OF THE SUITABILITY OF A PATIENT FOR A SCAN OF THE PATIENT'S HEART USING AN X-RAY COMPUTER TOMOGRAPH AND METHOD AND X-RAY COMPUTER TOMOGRAPH FOR SCANNING THE HEART OF A PATIENT

(75) Inventors: Thomas Allmendinger, Forcheim (DE); Heiko Mehldau, Nürnberg (DE); Thomas Seiler, Buckenhof (DE); Carsten Thierfelder, Pinzberg (DE)

(73) Assignee: Siemens Aktiengesellschaft, Munich (DE)

( * ) Notice: Subject to any disclaimer, the term of this patent is extended or adjusted under 35 U.S.C. 154(b) by 627 days.

(21) Appl. No.: 12/818,587

(22) Filed: Jun. 18, 2010

(65) Prior Publication Data
US 2010/0324434 A1 Dec. 23, 2010

(30) Foreign Application Priority Data
Jun. 22, 2009 (DE) .................. 10 2009 030 109

(51) Int. Cl.
*A61B 5/05* (2006.01)

(52) U.S. Cl.
USPC ........... 600/425; 600/407; 600/426; 600/427; 600/428; 600/429; 378/4; 378/11; 378/20

(58) Field of Classification Search
USPC ............... 600/407, 425, 426, 427, 428, 429; 378/4, 11–20
See application file for complete search history.

(56) References Cited

U.S. PATENT DOCUMENTS

| | | | |
|---|---|---|---|
| 5,935,069 A * | 8/1999 | Chandler et al. | 600/443 |
| 6,628,981 B2 * | 9/2003 | Baker et al. | 600/425 |
| 7,548,777 B2 | 6/2009 | Warmuth | |
| 2006/0287594 A1 | 12/2006 | Boese et al. | |
| 2009/0124892 A1 | 5/2009 | Bruder et al. | |

FOREIGN PATENT DOCUMENTS

| | | |
|---|---|---|
| DE | 102005012386 A1 | 9/2006 |
| DE | 102005027944 A1 | 1/2007 |
| DE | 102007051548 A1 | 6/2009 |

OTHER PUBLICATIONS

Russo et al., "How Fluent is Your Interface? Designing for International Users" Apr. 1993, Interchi '93, p. 342-347.*

* cited by examiner

*Primary Examiner* — James Kish
(74) *Attorney, Agent, or Firm* — Harness, Dickey & Pierce, P.L.C.

(57) ABSTRACT

A method is disclosed for assisting in determination of the suitability of a patient for a scan of the heart of the patient using an X-ray computer tomograph. In at least one embodiment of the method, a) an electrocardiogram of the patient is recorded; b) the electrocardiogram is evaluated by predicting the occurrence time of at least the immediately following R wave on the basis of at least four immediately consecutive R waves of the electrocardiogram which were measured last, and comparing this with the actual measured occurrence time of the next R wave; and c) wherein the quality of the prediction is visualized qualitatively. Further, in at least one embodiment, a device is disclosed including an ECG instrument and a computation device for carrying out the method. At least one embodiment of the invention furthermore relates to a method and a device for scanning the heart of a patient on the basis of a prediction of R waves.

18 Claims, 2 Drawing Sheets

METHOD AND DEVICE FOR ASSISTING IN DETERMINATION OF THE SUITABILITY OF A PATIENT FOR A SCAN OF THE PATIENT'S HEART USING AN X-RAY COMPUTER TOMOGRAPH AND METHOD AND X-RAY COMPUTER TOMOGRAPH FOR SCANNING THE HEART OF A PATIENT

PRIORITY STATEMENT

The present application hereby claims priority under 35 U.S.C. §119 on German patent application number DE 10 2009 030 109.7 filed Jun. 22, 2009, the entire contents of which are hereby incorporated herein by reference.

FIELD

At least one embodiment of the invention generally relates to a method and/or a device for assisting in determination of the suitability of a patient for a scan of the patient's heart using an X-ray computer tomograph, wherein a doctor is provided with a basis for the decision whether the scan is carried out or is better omitted. At least one embodiment of the invention furthermore generally relates to a method and an X-ray computer tomograph for scanning a patient' heart.

BACKGROUND

Patients with heart diseases, in so far as is medically necessary and expedient, are subjected to scans using X-ray computer tomographs in order to examine the heart, a scan being intended to mean recording a multiplicity of 2D X-ray projections of the heart from different projection directions, usually with an incremental advance of the heart or the patient relative to the X-ray recording system of the X-ray computer tomograph. The purpose of the examination is to generate high-quality and informative images of the heart, which often form the basis for a diagnosis.

Since the heart is a moving organ, when reconstructing slice images and 3D images of the heart, which is done on the basis of the recorded 2D X-ray projections of the heart, attempts are made to use only those 2D X-ray projections that have been recorded in the cardiac phase of the patient's cardiac cycle in which the heart has performed almost no movement, particularly in order to avoid motion artifacts in the reconstructed slice images and 3D images of the heart. In order to determine the cardiac cycle of the patient's heart, it is usual to record an electrocardiogram (ECG) of the patient's heart.

For producing slice images and 3D images of the heart, 2D X-ray projections of the heart are recorded over several cardiac cycles with parallel recording of the electrocardiogram, and subsequently only the 2D X-ray projections suitable for the reconstruction are selected on the basis of the electrocardiogram, for which reason this is also referred to as a retrospective method.

In an alternative procedure, 2D X-ray projections of the heart are likewise obtained over several cardiac cycles, but on the basis of an electrocardiogram recorded in parallel only if the heart is in a cardiac phase for which it performs almost no movement. This procedure has the advantage that the patient is exposed to a lower X-ray dose.

Obtaining 2D X-ray projections of the heart over several cardiac cycles has been or is necessary since not enough 2D X-ray projections from different projection directions of the patient's heart could be obtained with the previously available X-ray computer tomographs within only one resting phase of the patient's cardiac cycle, in order to reconstruct high-quality slice images and 3D images of the heart. The reason for this resides in the limited rotation speed of the gantry rotating around the patient and comprising the X-ray system, as well as the limited acceleration and adjustment speed of the patient table supporting the patient.

Recently, however, X-ray computer tomographs, in particular X-ray computer tomographs having two X-ray systems arranged on a gantry and offset by about 90°, have become available, with which it is possible to obtain enough 2D X-ray projections from different projection directions within the resting phase of only one cardiac cycle of a patient's heart, so that high-quality slice images and 3D images of the patient's heart can be reconstructed. Patients who are viable for a successful examination using such X-ray computer tomographs, however, are subject to certain physiological restrictions, particularly in relation to the duration of the cardiac cycle and the tolerable variance of the cardiac cycle.

SUMMARY

In at least one embodiment of the invention, a method and a device are provided, so as to provide a basis for a decision whether the scan can be carried out successfully in only one resting phase of a patient's part. Furthermore, in at least one embodiment of the invention, a suitable method and an X-ray computer tomograph are provided for scanning the patient's heart in only one resting phase of the heart.

According to at least one embodiment of the invention, a method is disclosed for assisting in determination of the suitability of a patient for a scan of the patient's heart using an X-ray computer tomograph.

At least one embodiment of the method is based on the idea that for the intended scan of the heart, in which the 2D X-ray projections are recorded from different directions of the patient's heart in the resting phase of only one cardiac cycle of the patient's heart in order to reconstruct slice images and/or 3D images of the heart, it is necessary to establish whether the patient intended for the scan, or the patient's heart, exhibits a suitable cardiac cycle and a tolerable variance of the cardiac cycle so that the scan can be carried out successfully within the resting phase of only one cardiac cycle of the patient. If the heart rate or the variance of the patient's cardiac cycle is too high, the patient is not suitable for said scan and an alternative scanning method should be selected.

In order to be able to record the 2D X-ray projections of the patient's heart in only one resting phase of the heart, it must be possible for the starting time of the scan in the resting phase of the patient's heart to be predicted comparatively stably. For this reason, in order to determine the heart rate and the cardiac cycle of the patient, an electrocardiogram of the patient's heart is initially recorded in a method step a).

This electrocardiogram is evaluated by predicting the occurrence time of at least the immediately following R wave on the basis of at least four immediately consecutive R waves of the electrocardiogram which were measured last, and comparing this with the actual measured occurrence time of the next R wave. From comparison of the result of the prediction and the measured occurrence of the next R wave, a quality of the prediction can be determined. If the prediction is in a predeterminable tolerance range, the prediction is acceptable and the patient's cardiac cycle is such that at least the occurrence time of the R wave following four previously measured R waves or three previously measured cardiac cycles or cycle lengths can be predicted for the patient in question with sufficient accuracy so that the starting time of the scan can also be established per se. This fact or the suitability in principle, or possibly the unsuitability, is finally visualized so that for example a doctor can make the decision about carrying out the scan while taking into account other aspects relating to the patient if appropriate.

According to a variant of at least one embodiment of the invention, the patient is requested to hold his breath while the electrocardiogram is being recorded, only that part of the electrocardiogram which is recorded while the patient has been holding his breath for two to five cardiac cycles and/or three to four seconds being employed for the evaluation. It has been found that holding the breath as a positive effect on the heart rate and the variability of the heart rate. Thus, when a patient is holding his breath, the heart rate is generally three to ten heart beats less than the heart rate encountered when the patient is breathing freely. The variance of the heart rate furthermore decreases when the breath is being held, which improves the stability of the prediction of R waves. Since immediately after he starts to hold his breath, depending on the patient, the heart rate does however increase for about two to five cardiac cycles, or when he is holding his breath it takes about three to four seconds until the patient's heart rate is equilibrated or stable, the part of the electrocardiogram which is recorded after this time is first waited for.

According to one embodiment of the invention, in method step b) the occurrence times of the immediately following $x(t+1)^{th}$ R wave and the $x(t+2)^{th}$ R wave are predicted on the basis of an $x(t-3)^{th}$, an $x(t-2)^{th}$, an $x(t-1)^{th}$ and an $x(t)^{th}$ immediately consecutive measured R wave of the electrocardiogram, and compared with the actual measured occurrence times of the immediately following $x(t+1)^{th}$ R wave and $x(t+2)^{th}$ R wave.

Preferably, method step b) is carried out repeatedly in order to determine the quality of the prediction. According to another embodiment of the invention, method step b) is carried out several times in succession or in an overlapping fashion in relation to the R waves, an advance by one R wave taking place each time it is carried out.

For example, the occurrence times of the immediately following fifth and sixth R waves are predicted on the basis of a first, a second, a third and a fourth immediately consecutive measured R wave of the electrocardiogram, and compared with the actual measured occurrence times of the immediately following fifth and sixth R waves. In continuation of at least one embodiment of the method, the occurrence times of the immediately following sixth and seventh R waves are predicted on the basis of the second, the third, the fourth and the fifth immediately consecutive measured R waves of the electrocardiogram, and compared with the actual measured occurrence times of the immediately following sixth and seventh R waves. Lastly, the occurrence times of the immediately following seventh and eighth R waves are predicted on the basis of the third, the fourth, the fifth and the sixth immediately consecutive measured R waves of the electrocardiogram, and compared with the actual measured occurrence times of the immediately following seventh and eighth R waves.

In this way, a plurality of predictions are obtained for the occurrence times of R waves, and by comparing these with the actual occurrence times of the respective R wave the quality of the prediction individually and/or the quality of the prediction in total can be determined and visualized.

According to a variant of at least one embodiment of the invention, a prediction of the occurrence time of an R wave is classed as adequate or acceptable if the difference between the time prediction and the actual measured occurrence time of the R wave is less than 5%.

According to one embodiment of the invention, the quality of the prediction or predictions is visualized green overall if the relevant predictions have predominantly been classed as adequate, and it is visualized red overall if the relevant predictions have predominantly been classed as too inaccurate. Visualization with the color green means that the patient in question is classed as suitable for the intended scan, since the occurrence times of R waves can be predicted comparatively stably. Visualization with the color red means that the patient in question is classed as not suitable for the intended scan. The final decision about carrying out the scan, however, lies with the doctor in charge.

At least one embodiment of the present invention is also directed to a device that has an ECG instrument and computation means, which are adapted to carry out one of the methods above. To this end, the computation devices are preferably provided with corresponding software or corresponding software modules, so that the method can be carried out in an automated fashion.

At least one embodiment of the invention is directed to a method for recording 2D X-ray projections of a patient's heart from different projection directions in the resting phase of only one cardiac cycle of the patient using an X-ray computer tomograph, wherein the patient's suitability for the recording of 2D X-ray projections of the patient's heart in the resting phase of only one cardiac cycle of the patient's heart is initially determined according to the one of the methods described above, an electrocardiogram of the patient's heart is obtained using an ECG instrument, the occurrence times of the immediately following fifth and sixth R waves are predicted on the basis of a first, a second, a third and a fourth immediately consecutive measured R wave of the patient's electrocardiogram, and wherein the start of the recording of the 2D X-ray projections of the patient's heart takes place in the predicted cardiac cycle lying between the predicted fifth and sixth R waves. According to at least one embodiment of the invention, the occurrence of the next but one cardiac cycle is thus predicted on the basis of four measured R waves or three measured cardiac cycles or cycle lengths, and the scan of the heart is started in the predicted cardiac cycle.

Preferably, the start of the scan, or the start of recording the 2D X-ray projections of the patient's heart, takes place at about 50% to 60% of the predicted cardiac cycle. According to a variant of at least one embodiment of the invention, the scan, or the recording of the 2D X-ray projections of the patient's heart, is ended at about 90% of the predicted cardiac cycle. Here, the resting phase of the heart lies between 50% and 90% of the predicted cardiac cycle.

According to one embodiment of the invention, at least one 2D slice image and/or a 3D data set of the patient's heart is reconstructed only on the basis of the 2D X-ray projections recorded in a resting phase of the patient's heart. In the resting phase of the heart, it is thus possible to record enough 2D X-ray projections so that high-quality 2D slice images and/or a high-quality 3D data set can be reconstructed.

At least one embodiment of the invention is also achieved by a device having an ECG instrument and an X-ray computer tomograph, wherein computation devices of the X-ray computer tomograph are adapted to carry out one of the methods described above with corresponding software.

BRIEF DESCRIPTION OF THE DRAWINGS

An example embodiment of the invention is represented in the appended schematic drawings, in which.

DETAILED DESCRIPTION OF THE EXAMPLE EMBODIMENTS

Figure 1:
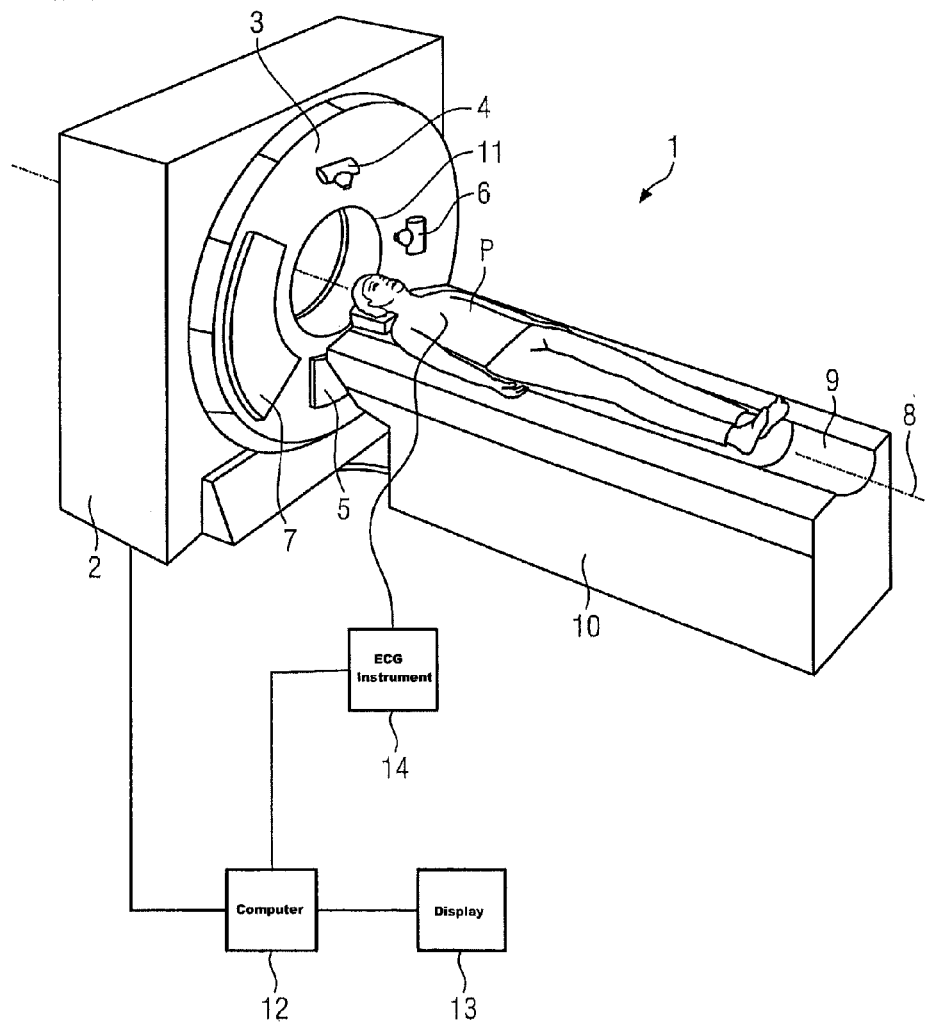
FIG. 1 shows an X-ray computer tomograph for carrying out a scan of a patient's heart.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an X-ray computer tomograph 1 which, in a housing 2, has a gantry 3 which can be rotated about a symmetry axis 8 relative to the housing 2 and on which two X-ray systems are arranged offset relative to one another by about 90°. The first X-ray system has an X-ray source 4 and an X-ray detector 5 lying opposite one another, and the second X-ray system has an X-ray source 6 and an X-ray detector 7 lying opposite one another. The central beam of the X-ray bundle coming from the first X-ray source 4 and the central beam of the X-ray bundle coming from the second X-ray source 6 intersect approximately at a 90° angle on the symmetry axis 8 of the X-ray computer tomograph 1. During operation, X-radiation travels from the X-ray source 4 in the direction of the X-ray detector 5 and X-radiation travels from the X-ray source 6 in the direction of the X-ray detector 7, this radiation being recorded by the X-ray detectors 5 and 7, respectively.

In the case of the present example embodiment of the invention, the patient support plate 9 of a patient table 10 of the X-ray computer tomograph 1 supports a patient P, from whose heart 2D X-ray projections are intended to be recorded from different projection directions in only one resting phase of the cardiac cycle of the patient P using the X-ray computer tomograph 1, in order to reconstruct 2D slice images and/or 3D images of the heart of the patient P. To this end, the patient support plate 9 is adjusted or moved so that the 2D X-ray projections of the heart of the patient P can be recorded for example in a spiral scan.

The computational processing of the 2D X-ray projections which are recorded using the two X-ray systems, or the reconstruction of slice images and/or 3D images on the basis of the 2D X-ray projections, is carried out using a schematically represented computer 12 of the X-ray computer tomograph 1, which slice images or 3D images can be represented on a display device 13.

The X-ray computer tomograph 1 may for example be a Somatom Definition Flash computer tomograph from Siemens AG, the gantry of which has a rotation time of about 0.28 seconds and the patient support plate of which has an adjustment speed of up to 43 cm/second.

Figure 2:
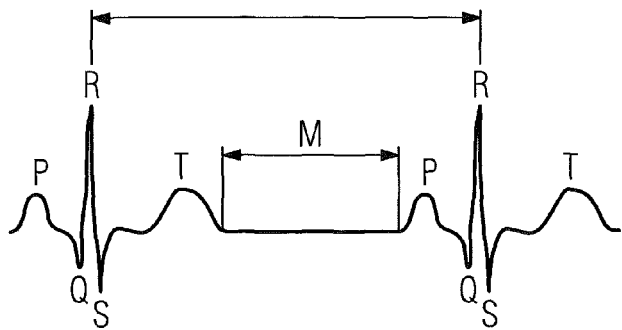
FIG. 2 shows a cardiac cycle of a human heart.

Regarding the cardiac cycle of a human recorded by an ECG instrument, as shown in FIG. 2, this has characteristic waves denoted by P, Q, R and T, and sections lying between the waves. Here, what is important is the time between two successive R waves and the section denoted by M between the T and P waves, which represents the phase of the heart in which it performs almost no movement and in which 2D X-ray projections of the heart are preferably recorded for imaging the heart.

The cardiac cycle of a healthy human is such that a full scan of the heart can be carried out in only one resting phase M of the cardiac cycle, for example using the Somatom Definition Flash computer tomograph from Siemens AG, this requiring only about 250 milliseconds with the Somatom Definition Flash. Specifically for patients with heart diseases, however, the cycle time may be shortened or the cardiac cycle may have a strong variability, so that before such a scan of a patient's heart it is necessary to ascertain the patient's suitability in principle for this type of scan. In particular, the purpose of this is to avoid scans of this type which cannot be carried out successfully, and therefore an unnecessary radiation dose for patients.

In the case of the present example embodiment of the invention, the patient P is therefore provided with ECG electrodes (not shown explicitly) and connected to an ECG instrument 14, which is linked to the computer 12 of the X-ray computer tomograph 1. An ECG of the heart of the patient P is recorded using the ECG instrument 14, and evaluated in order to assist in determining the suitability of the patient P for the scan in only one resting phase of the heart of the patient P using the X-ray computer tomograph 1.

After the start of recording the ECG using the ECG instrument 14, in the case of the present example embodiment of the invention the patient P is requested to hold his breath, the advantage of which is that the heart rate when the breath is being held is generally about three to ten heart beats less than the heart rate encountered when breathing freely. The variance of the heart rate furthermore decreases when the breath is being held. Before the evaluation of the ECG begins, after the instruction to hold his breath, about two to five cardiac cycles or about three to four seconds are furthermore waited until the heart rate of the patient P is equilibrated or stable.

In principle, it is also possible for the ECG when the patient P is breathing freely to be evaluated in relation to the suitability of the patient P for the scan, a scan is also possible when the patient P is breathing freely. Besides the associated positive aspects i.e. the aforementioned lower heart rate and the lower variance of the heart rate, however, holding the breath is an everyday established clinical working procedure which is also practiced in other examinations of patients using computer tomographs, for example for obtaining a topogram of the patient or in examinations in which contrast agents are applied, for which reason this procedure is described in the case of the present example embodiment.

Figure 3:
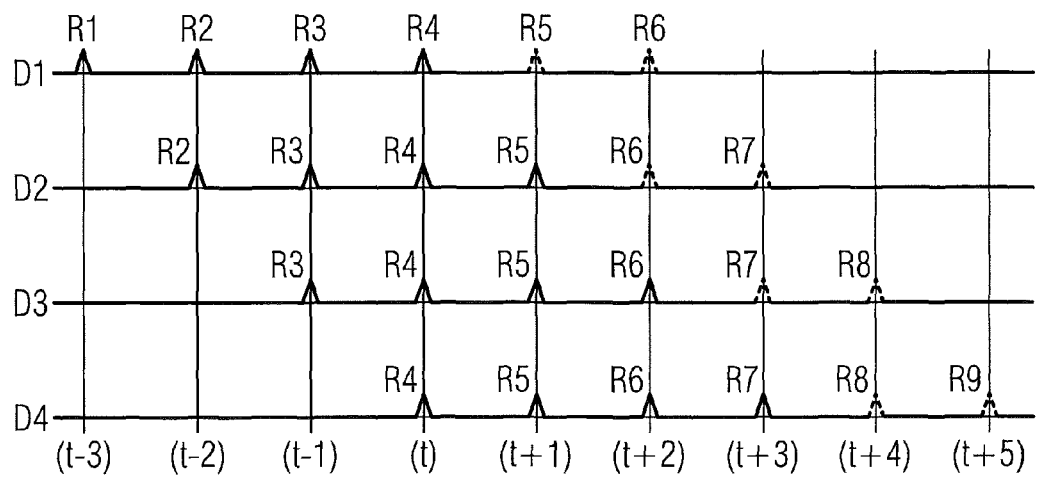
FIG. 3 shows an illustration of the prediction of R waves and FIG. 4 shows an illustration of the calculation of the scan start.

Once the two to five cardiac cycles and/or three to four seconds have elapsed after the patient has started to hold his breath, the software-controlled evaluation of the ECG of the patient P is carried out using the computer 12, which is provided with corresponding software. FIG. 3 illustrates the evaluation of the ECG in the case of the present example embodiment of the invention.

In the automatic software-controlled evaluation of the ECG, the occurrence time (t−3) of a first R wave R1, the occurrence time (t−2) of a second R wave R2, the occurrence time (t−1) of a third R wave R3 and the occurrence time (t) of a fourth R wave R4 are registered while recording the ECG. During the further recording of the ECG, the occurrence time of the fifth R wave R5 following the fourth R wave R4 and the sixth R wave R6 immediately chronologically following the fifth R wave R5 are predicted or determined on the basis of the four said times of the four registered R waves R1 to R4, or the three measured cardiac cycles or cycle lengths. The determination is carried out in the time interval between the occurrence of the fourth R wave R4 and the fifth R wave R5.

The determination of the cycle lengths or cycle times between the R waves R4 and R5, and R5 and R6, or the determination of the occurrence times of the R waves R5 and R6 on the basis of the determination of the cycle lengths or cycle times between the R waves R4 and R5, and R5 and R6, may be carried out with the aid of a median filter ME whose input values are the cycle times between the R waves R1 and R2, R2 and R3, and R3 and R4. When the cycle time determined using the median filter ME is added to the time of the last measured R wave R4, the prediction for the occurrence time of the R wave R5 is obtained, and when it is added twice the prediction for the occurrence time of the R wave R6 is obtained.

This determination can be made more precise by determining the linear trend of these three cardiac cycles in parallel with the aid of a linear regression. On the basis of this, a trend line with a slope a and an intercept b can be determined, and a standard deviation of the measured cycle times can be determined from the trend line. Taking into account a weight w which is based on the standard deviation and whose value lies between zero and one, in the present case the cycle lengths or cycle times between the R waves R4 and R5 are determined here as $C1=w*(b)+(1-w)*ME$, and between the R waves R5 and R6 as $C2=w*(a+b)+(1-w)*ME$. This gives the occurrence time of the R wave R5 as $R5=R4+C1$ and the occurrence time of the R wave R6 as $R6=R4+C1+C2$.

When the fifth R wave R5 is registered, its occurrence time is compared with the predicted occurrence time of the fifth R wave R5. If the difference between the predicted occurrence time of the fifth R wave R5 and the actual occurrence time of the fifth R wave R5 is less than 5%, the prediction is classed as adequate or acceptable.

Once the fifth R wave R5 has been registered, in the scope of the software-controlled evaluation of the patient's ECG the occurrence times of the sixth R wave R6 and the seventh R wave R7 are predicted as explained above on the basis of the respective occurrence times of the second R wave R2, the third R wave R3, the fourth R wave R4 and the fifth R wave R5.

Finally, when the occurrence time of the sixth R wave R6 is registered, two comparison values are available for it. In respect of a first run D1, the actual occurrence time of the sixth R wave R6 is compared with the time prediction of the occurrence of the sixth R wave R6 based on the R waves R1 to R4, and in respect of a second run D2 the actual occurrence time of the sixth R wave R6 is compared with the time prediction of the occurrence of the sixth R wave R6 based on the R waves R2 to R5. For both cases, whether the difference between the respective prediction and the actual occurrence time of the sixth R wave R6 is less than 5% is determined. This furthermore provides an estimate of the stability of the heart rate of the patient P, i.e. whether a comparatively reliable prediction of the next but one R wave is actually possible.

In the same way, further runs D3 and D4 or mutually overlapping predictions are carried out, an advance by one R wave that has occurred taking place each time a prediction is carried out. Thus, the occurrence times of the R waves R7 and R8 are predicted on the basis of the measured occurrence times of the R waves R3 to R6, the occurrence times of the R waves R8 and R9 are predicted on the basis of the measured occurrence times of the R waves R4 to R7, etc., and in each case checked in relation to their acceptance.

As a result of the method, the quality of the predictions in total is finally determined and visualized. If the predictions have predominantly been acceptable, the quality of the prediction is visualized with the color green or a green light, for example as a green traffic light, so as to indicate that the patient is classed as suitable for the intended scan. If the predictions have predominantly not been acceptable, the quality of the prediction is visualized with the color red or a red light, for example as a red traffic light, so as to indicate that the patient is classed as not suitable for the intended scan. The quality may respectively be displayed on the viewing instrument 13.

Taking into account further aspects relating to the patient, a doctor therefore has a basis for making a decision whether a scan, in which 2D X-ray projections of the heart of the patient P are recorded from different projection directions in only one resting phase of the heart, should be carried out for the patient P. If a topogram of the heart of the patient P has previously been recorded with the patient P holding his breath, the region of the heart which is scanned in the interval between two predicted R waves may be indicated graphically in the topogram.

When suitability of the patient P in principle for the scan has been established, and the decision for the scan has been made, the adjustments of the X-ray computer tomograph 1, for example the speed of the forward increment of the patient support plate 9, the rotation speed of the gantry 3 etc. are carried out individually for the scan of the patient P so that, on the basis of the currently recorded ECG of the patient P and the occurrence times of two R waves predicted on the basis of the ECG, the scan of the patient begins at about 50%-60% of the interval between the two predicted R waves and ends at about 90% of the interval between the two predicted R waves.

On the basis of four occurrence times of R waves, in the present case the occurrences of the following two R waves are thus predicted and the scan is carried out in the interval between the two predicted R waves. To this end, the patient support plate 9 must be accelerated promptly so that it has reached the established scan speed at the calculated time of the scan start.

Figure 4:
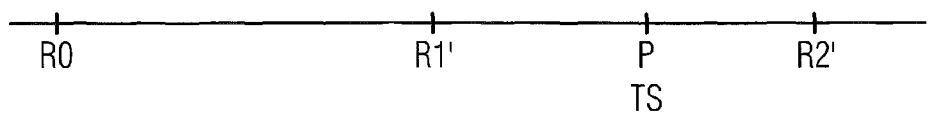

If, in the event that a patient exhibits a heart rate which is elevated but stable per se, the time for accelerating the patient support plate 9 up to the planned scan start at about 50%-60% of the interval between the two predicted R waves is not sufficient to bring the patient support plate 9 to the speed required for the scan, the start of the scan may also be shifted under software control into the interval between two R waves following the interval which has been determined. This will be illustrated briefly with the aid of FIG. 4. R0 is the time of the R wave measured last, R1' and R2' are the predicted times of the next two R waves, P is the desired start phase of the scan at about 60% of the interval between R1' and R2' and TT is the time which the patient support plate 9 needs in order to have reached its final speed or scan speed at the starting time TS of the scan. The scan start time is given as TS=R1'+P*(R2'−R1') and the start time derived therefrom for the patient support plate 9 is given as TP=TS−TT. If the time TP now lies before R0, the scan would not be possible with these parameters. In order to make the scan possible in spite of this, as already mentioned, the scan start is placed after R2' and the scan start time is selected as TS=R2'+C, where is a time delay.

The time delay C is given on the basis of the patient's current heart rate from a table which has been determined from empirical values, i.e. a particular heart rate is assigned a particular time delay C determined from empirical values.

The use of at least one embodiment of the invention has been described above in connection with the Somatom Definition Flash computer tomograph from Siemens AG. Embodiments of the invention may, however, also be used with other computer tomographs which are suitable for carrying out a scan of the heart within only one resting phase of a patient's heart, while being based on reliable predictions of two cardiac cycles.

The prediction of the occurrence times of R waves may be carried out merely by using a median filter, or in combination with the determination of a linear trend. The prediction may, however, be carried out using other mathematical methods, for example by way of an extrapolation.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for assisting in determination of the suitability of a patient for a scan of a heart of the patient in a resting phase of only one cardiac cycle of the patient's heart using an X-ray computer tomograph, the method comprising:
recording an electrocardiogram of the patient;
evaluating, by a processor, the electrocardiogram by predicting an occurrence time of at least an immediately following R wave based upon at least four immediately consecutive R waves of the electrocardiogram which were previously measured;
comparing, by the processor, the occurrence time with an actual measured occurrence time of the next R wave to obtain an accuracy of the prediction;
determining, by the processor, a quality of the prediction by comparing the accuracy with a threshold; and
displaying, by the processor, the quality of the prediction.

2. The method as claimed in claim 1, wherein the recording of the electrocardiogram is performed while the patient stops breathing, only a part of the electrocardiogram which is recorded while the patient has stopped breathing for at least one of two to five cardiac cycles and three to four seconds is used in the evaluating.

3. The method as claimed in claim 2, wherein in the evaluating, the occurrence times of the immediately following fifth and sixth waves are predicted on a basis of a first, a second, a third and a fourth immediately consecutive measured R waves of the electrocardiogram, and compared with the actual measured occurrence times of the immediately following fifth and sixth waves.

4. The method as claimed in claim 1, wherein in the evaluating, the occurrence times of immediately following fifth and sixth R waves are predicted on a basis of a first, a second, a third and a fourth immediately consecutive measured R waves of the electrocardiogram, and compared with the actual measured occurrence times of the immediately following fifth and sixth waves.

5. The method as claimed in claim 1, wherein the evaluating is carried out repeatedly in order to determine the quality of the prediction.

6. The method as claimed in claim 3, wherein the evaluating is carried out in an overlapping fashion in relation to the R waves, an advance by one R wave taking place each time the evaluating is carried out.

7. The method as claimed in claim 1, wherein a prediction of the occurrence time of an R wave is classed as adequate if a difference between the predicted time and the actual measured occurrence time of the R wave is less than 5%.

8. The method as claimed in claim 7, wherein the quality of the prediction is visualized green overall if the relevant predictions have predominantly been classed as adequate, and wherein the quality of the predictions is visualized red overall if the relevant predictions have predominantly been classed as too inaccurate.

9. A method for recording 2D X-ray projections of a heart of a patient from different projection directions in a resting phase of only one cardiac cycle of the patient using an X-ray computer tomograph, the method comprising:
determining a suitability of the patient, for recording of 2D X-ray projections of the heart of the patient in the resting phase of only one cardiac cycle of the heart of the patient, according to the method as claimed in claim 1;
obtaining an electrocardiogram of the patient using an ECG instrument;
predicting occurrence times of immediately following fifth and sixth R waves based upon a first, a second, a third and a fourth immediately consecutive measured R waves of the electrocardiogram of the patient; and
starting the recording of the 2D X-ray projections of the heart of the patient in the predicted cardiac cycle lying between the predicted fifth and sixth R waves.

10. The method as claimed in claim 9, wherein the start of the recording of the 2D X-ray projections of the heart of the patient takes place at about 50% to 60% of the predicted cardiac cycle.

11. The method as claimed in claim 10, wherein the recording of the 2D X-ray projections of the heart of the patient is ended at about 90% of the predicted cycle.

12. The method as claimed in claim 10, wherein the visualizing represents the suitability of the patient for a subsequent scan of the heart.

13. The method as claimed in claim 9, wherein the recording of the 2D X-ray projections of the heart of the patient is ended at about 90% of the predicted cardiac cycle.

14. The method as claimed in claim 9, wherein at least one of a 2D slice image and a 3D data set of the heart of the patient is reconstructed based on the 2D X-ray projections recorded in the resting phase of the heart of the patient.

15. A device, comprising:
an ECG instrument; and
an X-ray computer tomograph, wherein a computation device of the X-ray computer tomograph carries out the method as claimed in claim 9.

16. A non-transitory computer readable medium including a computer program product, the computer program product comprising instructions, which when executed on a computer device, causes the computer device to implement the method of claim 9.

17. A non-transitory computer readable medium including a computer program product, the computer program product comprising instructions, which when executed on a computer device, causes the computer device to implement the method of claim 1.

18. A device, comprising:
an electrocardiogram (ECG) instrument configured to record an electrocardiogram of a patient; and
a computation device configured to, record an electrocardiogram of a patient,
evaluate the electrocardiogram by predicting an occurrence time of at least an immediately following R wave based upon at least four immediately consecutive R waves of the electrocardiogram which were previously measured,
compare the occurrence time with an actual measured occurrence time of the next R, wave to obtain an accuracy of the prediction;
determining a quality of the prediction by comparing the accuracy with a threshold; and
displaying the quality of the prediction.

* * * * *